US012797506B2

(12) United States Patent
Okuno

(10) Patent No.: US 12,797,506 B2
(45) Date of Patent: Nov. 17, 2026

(54) PAIN TREATMENT AGENT

(71) Applicants: Medical Corporation Yuyukai, Tokyo (JP); ALIVIO JAPAN CORPORATION, Tokyo (JP)

(72) Inventor: Yuji Okuno, Tokyo (JP)

(73) Assignees: Medical Corporation Yuyukai, Tokyo (JP); ALIVIO JAPAN CORPORATION, Tokyo (JP)

( * ) Notice: Subject to any disclaimer, the term of this patent is extended or adjusted under 35 U.S.C. 154(b) by 553 days.

(21) Appl. No.: 18/261,677

(22) PCT Filed: Feb. 1, 2022

(86) PCT No.: PCT/JP2022/003896

§ 371 (c)(1),
(2) Date: Jul. 17, 2023

(87) PCT Pub. No.: WO2022/163869

PCT Pub. Date: Aug. 4, 2022

(65) Prior Publication Data

US 2024/0238475 A1 Jul. 18, 2024

(30) Foreign Application Priority Data

Feb. 1, 2021 (JP) ................................ 2021-014467
Dec. 28, 2021 (JP) ................................ 2021-215173

(51) Int. Cl.

| | |
|---|---|
| ***A61L 24/00*** | (2006.01) |
| ***A61K 9/00*** | (2006.01) |
| ***A61K 9/14*** | (2006.01) |
| ***A61K 31/198*** | (2006.01) |
| ***A61K 31/407*** | (2006.01) |
| ***A61P 23/02*** | (2006.01) |

(52) U.S. Cl.

CPC ........ *A61L 24/0015* (2013.01); *A61K 9/0019* (2013.01); *A61K 9/14* (2013.01); *A61K 31/198* (2013.01); *A61K 31/407* (2013.01); *A61P 23/02* (2018.01); *A61L 2300/204* (2013.01); *A61L 2300/214* (2013.01); *A61L 2300/402* (2013.01); *A61L 2400/04* (2013.01); *A61L 2400/06* (2013.01)

(58) Field of Classification Search

None
See application file for complete search history.

(56) References Cited

FOREIGN PATENT DOCUMENTS

| | | | |
|---|---|---|---|
| JP | 6856809 | B1 | 4/2021 |
| WO | WO 2018/218208 | A | 11/2018 |

OTHER PUBLICATIONS

Okuno et al., Midterm Clinical Outcomes and MR Imaging Changes after Transcatheter Arterial Embolization as a Treatment for Mild to Moderate Radiographic Knee Osteoarthritis Journal of Vascular and Interventional Radiology, 2017, pp. 1-8 (Year: 2017).*

TheNew York Hand and Wrist Center, Osteoarthritis of the Hand, Aug. 3, 2016, https://web.archive.org/web/20160803050538/https://www.handsurgeonsnewyork.com/osteoarthritis-of-the-hand/ (Year: 2016).*

Mackay, Rate of Drainage of the Blood Vessels of the Limbs by Gravity, J Appl Physiol. Sep. 1955;8(2):169-72. doi: 10.1152/jappl.1955.8.2.169. (Year: 1955).*

International Search Report of the International Searching Authority, mailed on Mar. 22, 2022, from International Application No. PCT/JP2022/003896, filed on Feb. 1, 2022. 5 pages.

Written Opinion of the International Searching Authority, mailed on Mar. 22, 2022, from International Application No. PCT/JP2022/003896, filed on Feb. 1, 2022. 5 pages.

International Preliminary Report on Patentability of the International Preliminary Examining Authority, dated May 19, 2023, from International Application No. PCT/JP2022/003896, filed on Feb. 1, 2022. 11 pages.

Yuji Okuno, "Pain in Heberden's node was caused by moyamoya blood vessels" Wani Books, Feb. 22, 2020, pp. 9.

Okuno, Y. et al., "Clinical Outcomes of Transcatheter Arterial Embolization for Adhesive Capsulitis Resistant to Conservative Treatment" Journal of Vascular and Interventional Radiology. 2017, vol. 28, pp. 161-167, ISSN 1051-0043. Published on Dec. 19, 2016.

Okuno, Y. et al., "Midterm Clinical Outcomes and MR Imaging Changes after Transcatheter Arterial Embolization as a Treatment for Mild to Moderate Radiographic Knee Osteoarthritis Resistant to Conservative Treatment" Journal of Vascular and Interventional Radiology. 2017, vol. 28, pp. 995-1002, ISSN 1051-0043, Published on Mar. 29, 2017.

Chen, Y. et al., "Transarterial chemoembolization for pain relief in patients with hypervascular painful metastatic spinal tumors refractory to percutaneous vertebroplasty", Journal of Cancer Research and Clinical Oncology, vol. 139: 1343-1348 (2013).

International Search Report and Written Opinion of the International Searching Authority, mailed on Aug. 17, 2021, from International Application No. PCT/JP2021/025464, filed on Jul. 6, 2021. 7 pages.

Okuno, Y. et al., "Pathological neoangiogenesis depends on oxidative stress regulation by ATM", Nature Medicine, Published on Jul. 15, 2012, vol. 18 (8), pp. 1208-1216 (2012).

(Continued)

*Primary Examiner* — Anna R Falkowitz
*Assistant Examiner* — Edwin Coleman Mitchell
(74) *Attorney, Agent, or Firm* — HoustonHogle LLP

(57) ABSTRACT

The present invention addresses the problem of providing a means for treating pain in the hands or feet, which can be performed in a safer manner and works by embolizing abnormal capillary vessels. The present invention provides a treatment agent for pain in the hands or feet, wherein: the pain treatment agent contains a particulate embolic material having an average particle size of 10 to 200 μm; the pain treatment agent is employed by being injected into an artery in a hand or a foot; and the administration of the pain treatment agent is completed on the basis of confirmation of at least one predetermined phenomenon.

19 Claims, No Drawings

(56) References Cited

OTHER PUBLICATIONS

Matsumaru, Y., “Anatomy of the Spinal Vessels and Embolization Therefrom” (Basic vascular anatomy of the spinal cord), Niche Neuro-Angiology Conference 2012, “<URL:http://nnac.umin.jp/nnac/di6huipuroguramu_files/Matsumaru.pdf>”, Published on May 26, 2012, Section 3, lines 20-28. 14 Pages.

US Office Action, mailed on Jul. 22, 2025, from U.S. Appl. No. 18/041,415, filed Feb. 13, 2023. 14 pages.

* cited by examiner

PAIN TREATMENT AGENT

RELATED APPLICATIONS

This application is a § 371 National Phase Application of International Application No. PCT/JP2022/003896, filed on Feb. 1, 2022, now International Publication No. WO 2022/163869, published on Aug. 4, 2022, which International Application claims priority to Japanese Application No. 2021-215173, filed on Dec. 28, 2021, and Japanese Application No. 2021-014467, filed on Feb. 1, 2021, the teachings of which are incorporated herein by reference in their entirety.

TECHNICAL FIELD

The present invention relates to a pain treatment agent.

BACKGROUND ART

As a pain occurring in an upper limb or a lower limb, pains caused by various diseases (Heberden's nodule and plantar fasciitis) are known.

Although the causes of such an upper limb or lower limb pain have been unknown for many years, the inventor has conducted extensive research and has found that abnormal blood flow due to an increase in abnormal capillary vessels (known as "problematic vessels" or "problem vessels") is a cause of the pain (for example, Non-Patent Document 1). Such abnormal capillary vessels are caused by nerve growth and the like. Based on this, the inventor has found a method of treating pain by delivering an embolic material (imipenem/cilastatin particles) into an abnormal capillary vessel to thereby embolize the abnormal capillary vessel and normalize the blood flow.

Non-Patent Document 1: Yuji Okuno; "HEBAHDEN KESSETSU NO ITAMIWA MOYAMOYAKEKKAN GA GENIN DATTA (PAIN OF HEBERDEN'S NODULE WAS CAUSED BY MOYAMOA VESSELS)," 2020, WANI BOOKS

DISCLOSURE OF THE INVENTION

Problems to be Solved by the Invention

However, there is a further need for technology that enables a safer method for treating upper limb or lower limb pain by embolizing an abnormal capillary vessel.

The present invention has been made in view of circumstances mentioned above, and an object thereof is to provide a more safely practicable means for treating upper limb or lower limb pain by embolizing an abnormal capillary vessel.

Means for Solving the Problems

The present inventor has found that, in the treatment of upper limb or lower limb pain by embolizing an abnormal capillary vessel, the above-mentioned problem can be solved by setting the time point at which the administration of the embolic material is terminated to a specific timing, thereby arriving at completion of the present invention. More specifically, the present invention provides the following.

(1) In a pain therapeutic agent for an upper limb or a lower limb according to a first aspect of the present invention, the pain therapeutic agent including a particulate embolic material having an average particle size of 10 μm or more and 200 μm or less, in which the pain therapeutic agent is used by injection administration into an artery of the upper limb or the lower limb, and the administration of the pain therapeutic agent is terminated based on confirmation of any one or more of the following (A) to (D):

(A) heat sensation at a pain site;

(B) pain different from the pain at the pain site;

(C) discoloration of the skin of the pain site; and (D) detection of the embolic material at the pain site in an X-ray image of Roentgen.

(2) According to a second aspect of the present invention, in the pain therapeutic agent as described in the first aspect, the upper limb is an entirety from a wrist to fingertips or a part thereof.

(3) According to a third aspect of the present invention, in the pain therapeutic agent as described in the first aspect, the upper limb is an entirety from a shoulder to a wrist or a part thereof.

(4) According to a fourth aspect of the present invention, in the pain therapeutic agent as described in the first aspect, the lower limb is an entirety from an ankle to toes or a part thereof.

(5) According to a fifth aspect of the present invention, in the pain therapeutic agent as described in the first aspect, the lower limb is an entirety from a hip joint to an ankle or part thereof.

(6) According to a sixth aspect of the present invention, in the pain therapeutic agent as described in any one of the first to fifth aspects, the pain is a pain arising from one or more selected from the group consisting of Heberden's nodule, CM arthropathy, Bouchard's nodule, spring finger, plantar apoeurostis, Morton disease, and hallux valgus.

(7) According to a seventh aspect of the present invention, in the pain therapeutic agent as described in any one of the first to fifth aspects, the pain is a pain arising from one or more selected from the group consisting of rheumatoid arthritis, humerus lateralis epicondylitis (tennis elbow), humerus medial epicondylitis (golf elbow), medial collateral ligament injury, osteochondritis dissecans, elbow synovial plica disorder, humerus medial epicondylus epiphyseal line dysraphism, olecranon epiphyseal line dysraphism, humerus fatigue fracture, radial fatigue fracture, ulnar fatigue fracture, deformed elbow arthritis, elbow-joint synovial inflammation, carpal tunnel syndrome, TFCC injury, tenosynovitis, gout, Achilles tendinitis, external tibial bone painful, foot joint synovitis, knee osteoarthritis, patellar tendinitis (jumper's knee), iliotibial band syndrome (runner's knee), pes anserine bursitis, patellofemoral syndrome, infrapatellar fat pad inflammation, synsprint, a pain after artificial joint replacement surgery, Osgood disease, and fatigue fracture.

(8) According to an eight aspect of the present invention, in the pain therapeutic agent as described in any one of the first to seventh aspects, the injection administration is performed in a state in which a blood flow to an affected area is tilted toward a direction of gravity rather than a horizontal plane.

Effects of the Invention

The present invention provides a more safely practicable means for treating an upper limb or lower limb pain by embolizing an abnormal capillary vessel.

PREFERRED MODE FOR CARRYING OUT THE INVENTION

Although embodiments of the present invention will be described hereafter, the present invention is not limited thereto.

<Pain Treatment Agents>

The pain treatment agent (hereinafter, also referred to as a "therapeutic agent of the present invention") according to the present invention is a therapeutic agent for upper limb or lower limb pain, and includes a particulate embolic material having an average particle size of 10 μm or more and 200 μm or less. The pain therapeutic agent is used by injection administration to an artery of the upper limb or the lower limb, and the administration of the therapeutic agent is terminated based on confirmation of any one or more of the following (A) to (D):

(A) heat sensation at a pain site;

(B) a pain different from the pain at the pain site;

(C) discoloration of the skin of the pain site; and (D) detection of the embolic substance at the pain site in X-ray images of Roentgen.

As described above, the present inventor has developed a method of treating upper limb or lower limb pain, the method including injecting an embolic material into an abnormal capillary vessel to embolize the abnormal capillary vessel to normalize the blood flow. However, in conventional methods, there are cases where a phenomenon of abnormal capillaries clogging is incomplete for some reason, or swelling of an affected area occurs. There is, therefore, room for improvement in both the therapeutic efficacy and safety.

Thus, as a result of further research by the present inventor, it has been found that an appropriate amount of embolic material can be administered to an abnormal capillary vessel by referring to the above-mentioned (A) to (D) with respect to the timing of the administration end of the embolic material, a result of which the effect of treating upper limb or lower limb pain can be safely exerted.

The recitation "treating a pain" as used herein refers to relieving or fully eliminating a pain.

In the present invention, the "upper limb or lower limb" refers to the whole or a part of the upper limb or the whole or a part of the lower limb in which a pain is occurring.

In the present invention, the "upper limb" is an entirety from the shoulder to the fingertips or a part thereof (for example, an entirety from the shoulder to the wrist or a part thereof, an entirety of a so-called arm or a part thereof, and an entirety from the wrist to the fingertips or a part thereof).

In the present invention, the "lower limb" is an entirety from the hip joint to the toes or a part thereof (for example, an entirety from the hip joint to the ankle or a part thereof, and an entirety from the ankle to the toes or a part thereof).

The "upper limb or lower limb pain" as used herein indicates any pain that occurs in the upper limb or lower limb. A site where the pain is occurring or a disease that causes the pain is not particularly limited.

From the viewpoint that the therapeutic agent of the present invention easily exerts the effect thereof, the upper limb pain may be pain arising from at least one selected from the group consisting of Heberden's nodule, CM arthritis, Bouchard's nodule, spring finger, rheumatoid arthritis, humerus lateralis epicondylitis (tennis elbow), humerus medial epicondylitis (golf elbow), medial collateral ligament injury, osteochondritis dissecans, elbow synovial plica disorder, humerus medial epicondylus epiphyseal line dysraphism, olecranon epiphyseal line dysraphism, humerus fatigue fracture, radial fatigue fracture, ulnar fatigue fracture, deformed elbow arthritis, elbow-joint synovial inflammation, carpal tunnel syndrome, TFCC injury, and tenosynovitis. The type of these pains can be identified by diagnosis by a doctor.

From the viewpoint that the therapeutic agent of the present invention easily exerts an effect thereof, the lower limb pain may be a pain arising from at least one selected from the group consisting of plantar apoeurostis, Morton disease, hallux valgus, rheumatoid arthritis, gout, Achilles tendinitis, external tibial bone painful, foot joint synovitis, knee osteoarthritis, patellar tendinitis (jumper's knee), iliotibial band syndrome (runner's knee), pes anserine bursitis, patellofemoral syndrome, infrapatellar fat pad inflammation, synsprint, a pain after artificial joint replacement surgery, Osgood disease, and fatigue fracture. The type of these pains can be identified by diagnosis by a doctor.

Hereinafter, the configuration of the therapeutic agent of the present invention will be described in detail.

(Embolic Material)

As the embolic material, a particulate material having an average particle size of 10 μm or more and 200 μm or less is used.

The phrase "embolic material" as used herein means a material capable of blocking a blood flow in an artery.

An average particle diameter of the embolic material can be appropriately adjusted depending on a diameter, etc. of the artery to be embolized.

From the viewpoint that the artery to be embolized is easily embolized, a lower limit of the average particle diameter of the embolic material is preferably 2 μm or more and more preferably 5 μm or more.

From the viewpoint of avoiding embolizing an unintended artery other than the abnormal capillary vessel or of easiness of delivery to the artery to be embolized, an upper limit of the average particle diameter of the embolic material is preferably 100 μm or less and more preferably 50 μm or less.

The "average particle diameter" as used herein indicates an average value of particle size distribution and is determined using a laser diffraction-type particle size distribution measuring device (e.g., "SALD" series, manufactured by SHIMADZU CORPORATION).

The shape of the embolic material is not particularly limited, but may be amorphous, spherical, rectangular, etc.

The embolic material is not particularly limited as long as it can block a blood flow in an artery and does not adversely affect a living body.

A material of the embolic material may be a material sparingly soluble in blood at a body temperature (e.g., 35 to 39° C.), in particular, imipenem/cilastatin, etc. However, from the viewpoint of preventing a normal blood vessel from being embolized when the embolic material unintentionally enters a normal blood vessel, the embolic material may also be a material temporarily sparingly soluble in blood at a body temperature (e.g., 35 to 39° C.) but eventually soluble in the blood at the body temperature.

(Form of Therapeutic Agent)

The therapeutic agent of the present invention is an agent to be used by injection administration to an upper limb or lower limb artery. Therefore, the therapeutic agent of the present invention may include, in addition to the embolic material, a medium that can be administered to an artery of a living body (physiological buffer, sterile water, saline, a medium, a contrast agent) and an optional component that may be included in injection agents if needed as long as the embolizing effect of the embolic material is not impaired.

The form of the therapeutic agent of the present invention may be an injection agent. The configuration of the injection is not particularly limited, but any configuration may be adopted that allows the injection to be administered into the upper limb or lower limb skin of a target of the administration, using an injection needle. Normally, the injection includes an injection needle (Surflo indwelling needle, or the like), a syringe or the like, and the embolic material or the like is filled in the syringe.

When the therapeutic agent of the present invention is administered, angiography may be performed in order to identify an administration site of the therapeutic agent. Moreover, a contrast agent may be used in combination with the embolic material of the present invention for the angiography. The type of the contrast agent is not particularly limited, but iohexol or the like may be used. It should be noted that the contrast agent may be included in the therapeutic agent of the present invention (that is, the contrast agent may be administered simultaneously with the embolic material) or may be administered separately from the therapeutic agent of the present invention. When the contrast agent is administered separately from the therapeutic agent of the present invention, the order of administration is not particularly limited, but preferably the contrast agent is administered first from the viewpoint of easiness of identification of the administration site.

At the time of administration of the therapeutic agent of the present invention, the following operations may be performed: puncture of the artery with a Surflo indwelling needle under ultrasound guidance, confirmation of reverse blood of an inner needle of the Surflo indwelling needle, pulling out of the inner needle, and connecting the outer cylinder and a syringe filled with the embolic material. Puncturing under ultrasound guidance is effective in preventing damages to nerves in the vicinity of the artery.

(Administration Site)

The therapeutic agent of the present invention is administered to any upper limb or lower limb artery which can be punctured with an injection needle.

Examples of upper limb arteries include a brachial artery, a radial artery, and an ulnar artery.

Examples of lower limb arteries include a femoral artery (such as superficial femoral artery), a popliteal artery, a posterior tibial artery, and a dorsalis pedis artery.

From the viewpoint that the embolic material can be efficiently administered to the abnormal capillary vessel (problematic vessels), the administration site is preferably an artery that feeds the pain site. The "artery that feeds the pain site" may be specifically an artery that is distributed within 10 cm upstream from the pain site.

When the upper limb pain is a pain arising from Heberden's nodule, CM arthritis, or spring finger, it is preferred to administer the pain therapeutic agent to an artery at a site away from a wrist wrinkle (the thickest wrinkle between the palm and the wrist) in the lateral direction by two fingers (about 4 cm) toward the elbow. It should be noted that a site closer to the wrinkles of the wrist than to the administration site is a site that is sensitive to stimulation, and the possibility that complex regional pain syndrome (CRPS) may occur due to the stimulation by the administration can increase. Therefore, it is preferable not to set the site as the administration site.

When the upper limb pain is Heberden's nodule, CM arthritis, Bouchard's nodule, spring finger, rheumatoid arthritis, humerus lateralis epicondylitis (tennis elbow), humerus medial epicondylitis (golf elbow), medial collateral ligament injury, osteochondritis dissecans, elbow synovial plica disorder, humerus medial epicondylus epiphyseal line dysraphism, olecranon epiphyseal line dysraphism, humerus fatigue fracture, radial fatigue fracture, ulnar fatigue fracture, deformed elbow arthritis, elbow-joint synovial inflammation, carpal tunnel syndrome, TFCC injury, or tenosynovitis, the brachial artery which flows into the affected area may be set as the administration site. When the brachial artery is set as the administration site, the puncture site is preferably set at the level of the elbow joint (the elbow joint and its peripheral site).

When the lower limb pain is a pain arising from plantar aponeurositis, administration to the posterior tibial artery is preferred. In such a case, since blood vessels are distributed from the vicinity of the puncture site to the affected area, a dorsalis pedis artery need not be compressed.

When the lower limb pain is a pain arising from Morton's disease, it is preferred to administer the pain therapeutic agent to either the posterior tibial artery or the dorsalis pedis artery (preferably a larger artery in size). In such a case, after puncturing, the embolic material is injected while pressing the posterior tibial artery and the dorsalis pedis artery with a finger, whichever is not punctured (that is, when the posterior tibial artery is punctured, the dorsalis pedis artery is pressed, and when the dorsalis pedis artery is punctured, the posterior tibial artery is pressed), whereby the embolic material easily reaches the affected area by the inflow pressure from the opposite side.

When the lower limb pain is pain arising from hallux valgus, administration to the dorsalis pedis artery is preferred. In such a case, the embolic material can easily reach the affected area if administration is performed while pressing the posterior tibial artery after puncture.

In a case where the lower limb pain is plantar apoeurostis, Morton disease, hallux valgus, rheumatoid arthritis, gout, Achilles tendinitis, external tibial bone painful, foot joint synovitis, knee osteoarthritis, patellar tendinitis (jumper's knee), iliotibial band syndrome (runner's knee), pes anserine bursitis, patellofemoral syndrome, infrapatellar fat pad inflammation, synsprint, pain after artificial joint replacement surgery, Osgood disease, or fatigue fracture, arteries (a femoral artery, such as a superficial femoral artery) which flow into the affected area may be set as the administration site.

When the lower limb pain is knee osteoarthritis, patellar tendinitis (jumper's knee), iliotibial band syndrome (runner's knee), pes anserine bursitis, patellofemoral syndrome, infrapatellar fat pad inflammation, synsprint, a pain after artificial joint replacement surgery, Osgood disease, or fatigue fracture, it is preferred to set the popliteal artery (e.g., a popliteal artery at knee joint level) as the administration site.

When the lower limb pain is rheumatoid arthritis, gout, Achilles tendinitis, external tibial bone painful, or foot joint synovitis, it is preferred to set the dorsalis pedis artery and/or posterior tibial artery as the administration site.

The embolic material is preferably administered to the upper limb or lower limb in a state in which the blood flow from the administration site to the affected area is tilted toward the direction of gravity rather than the horizontal plane (a state of being tilted preferably by 20° or more and more preferably 45° or more with respect to the horizontal plane) regardless of the administration site or the type of disease. By such administration, the embolic material and contrast agent (if used) having a higher specific gravity than blood are likely to be more efficiently distributed to the affected area by gravity. This effect is particularly preferred in the present invention, because the present invention relates to injection administration in which the delivery ratio to the affected area is more likely to be lower than in catheter administration.

When the affected area is an upper limb, as a method of tilting the blood flow from the administration site toward the affected area, toward the direction of gravity, the following methods can be exemplified.

The entirety of the upper limb (for example, from the wrist to the fingertips) is tilted toward the direction of gravity rather than the horizontal plane.

The blood vessels of the upper limb or the fingers are tilted in the direction of gravity by adjusting the patient's limb position (the angle of joint).

When the affected area is a lower limb, as a method of tilting the blood flow from the administration site toward the affected area, toward the direction of gravity, the following methods can be mentioned.

The entirety of the lower limb (for example, from the ankle to the toes) is tilted toward the direction of gravity from the horizontal plane.

To have the patient assume the prone position.

To have the patient assume the side lying position, with the pain site down.

To have the patient bend the knee in which a pain is occurring.

Regardless of the type of pain, it is preferred to puncture the administration site (artery) under ultrasound guidance. For example, since the ulnar artery is adjacent to an ulnar nerve and the posterior tibial artery is adjacent to a posterior tibial nerve, if puncture is performed under ultrasound guidance, nerve damage can be more reliably prevented.

(Dosage, etc.)

The administration rate and the administration frequency of the therapeutic agent of the present invention can be appropriately set according to the condition of the patient (age, weight, severity of symptoms, etc.). The dosage of the therapeutic agent of the present invention varies depending on the timing of the end of administration, and is not particularly limited.

(Timing of Administration End)

The technical feature of the present invention is that the time point at which the administration of the embolic material is terminated is set to a specific timing. Specifically, after the start of administration of the therapeutic agent of the present invention, the administration is terminated based on the confirmation of any one or more of the following (A) to (D).

(A) Heat sensation at a pain site;

(B) Pain different from the pain at the pain site;

(C) Discoloration of the skin of the pain site; and (D) Detection of the embolic material at the pain site in an X-ray image of Roentgen.

The "heat sensation at a pain site" indicates that, after administration of the therapeutic agent of the present invention, the patient feels feverish at the pain site as compared to before the administration of the therapeutic agent of the present invention. Whether or not heat sensation at the pain site has occurred can be determined based on patient's statement.

The "pain different from the pain at the pain site" indicates that, after administration of the therapeutic agent of the present invention, the patient feels pain different from the pain previously felt, as compared to before the administration of the therapeutic agent of the present invention. Examples of such pain include a tingling sensation, a prickling sensation, and a feeling of heaviness. Whether or not pain different from the pain at the pain site has occurred can be determined based on the patient's statement.

The "discoloration of the skin at the pain site" indicates that the color of the skin at the pain site changes after administration of the therapeutic agent of the present invention as compared to before the administration of the therapeutic agent of the present invention. Examples of the discoloration include a color change in which, immediately after the administration, the skin turns pale white, and thereafter turns red. Whether or not discoloration of the skin at the pain site has occurred can be determined based on the appearance.

The "detection of the embolic material at a pain site in an X-ray image of Roentgen" indicates confirmation of the presence of the embolic material at a pain site from an X-ray image of Roentgen. When such detection is performed, the therapeutic agent of the present invention is preferably used in combination with a contrast agent.

The time interval from the time at which any one or more of phenomena (A) to (D) are confirmed to the time at which the administration of the embolic material is terminated is not particularly limited so long as the time interval is based on the time at which any one or more of the phenomena (A) to (D) is confirmed; however from the viewpoint of suppression of side effects, the time interval is preferably short. More specifically, it is preferable to terminate the administration immediately after the time at which one or more of the phenomena (A) to (D) is confirmed.

"Immediately after the time at which one or more of the phenomena (A) to (D) is confirmed" may specifically preferably be within 50 seconds, more preferably within 30 seconds, specifically within 15 seconds, within 10 seconds, or within 5 seconds.

The administration of the embolic material may be terminated on the basis of confirmation of one of (A) to (D), or confirmation of two or more of (A) to (D). However, in a case in which the administration of the embolic material is terminated on the basis of the confirmation of two or more phenomena, from the viewpoint of preventing an excessive dosage, it is preferable that the time period from the time point at which the first phenomenon occurs to the time point at which the last phenomenon occurs is as short as possible (preferably within 1 minute).

The end of administration of the therapeutic agent of the present invention is performed by any operation capable of terminating the injection of the therapeutic agent into the administration site. As such an operation, for example, pulling out the outer cylinder from the administration site and performing compression hemostasis can be exemplified.

<Therapeutic Effect of Therapeutic Agent of Present Invention>

The therapeutic agent of the present invention allows treatment of an upper limb or lower limb pain to be safely performed by embolizing an abnormal capillary vessel. For example, according to the therapeutic agent of the present invention, by terminating the administration of the embolic material at the above-described timing, the pain treating effect can be achieved while appropriately preventing excessive administration of the embolic material and outcomes thereof, including delayed pain, necrotic color tone change, swelling of the affected area, and the like.

The therapeutic effect of the therapeutic agent of the present invention can be evaluated by any method for evaluating pain. Examples thereof include a method based on "numerical rating scale (NRS) score" and a method in which a patient subjectively answers the degree of pain relief ("Patients Global Impression of Change").

EXAMPLES

Hereinafter, the present invention will be described with reference to Examples in more detail, but the present invention is not limited to these Examples.

<Preparation of Embolic Material Etc.>

In this Example, imipenem/cilastatin (product name "Primaxin", manufactured by Merck & Co., Inc.) was used as an embolic material. This embolic material had an average particle diameter of 70 μm or less as measured by a laser diffraction-type particle size distribution measuring device ("SALD" series, manufactured by SHIMADZU CORPORATION). The embolic material was prepared as a 1 g/10 ml aqueous solution.

In this Example, Iopaque (manufactured by Fuji Pharmaceutical Co., Ltd.) was used as a contrast agent. The contrast agent was used as an admixture with the embolic material. A mixing ratio (mass ratio of active ingredients) was set at 10 mL of the contrast agent with respect to 1 g of the embolic material.

Example 1-1: Treatment of Upper Limb Pain

The embolic material was administered by the following method to patients having Heberden's nodule (corresponding to a hand pain), to confirm an effect thereof.

(1) Setting of Administration Site of Embolic Material

The artery at a site away from a wrist wrinkle (the thickest wrinkle between the palm and the wrist) in the lateral direction by two fingers (about 4 cm) toward the elbow was set as the administration site. This site corresponds to the artery that feeds the pain site. It should be noted that a site closer to the wrinkles of the wrist than to the administration site is a site that is sensitive to stimulation, and the possibility of the complex regional pain syndrome (CRPS) occurring due to the stimulation by the administration can increase. Therefore, the site was not set as the administration site.

(2) Puncture to Administration Site (Artery)

The radial and ulnar arteries were observed with ultrasound waves and the vicinity of the administration site (artery) was anesthetized under ultrasound guidance. After the anesthetic was applied, the artery was punctured with a Surflo indwelling needle (24 G×19 mm) under ultrasound guidance. It should be noted that the ultrasound guidance was performed because there would have been a possibility of damaging nerves in the vicinity of the artery if the puncture had not been performed under ultrasound guidance. In particular, since the ulnar artery is adjacent to the ulnar nerve, it was effective to perform puncture under ultrasound guidance to prevent nerve damage. After puncturing the artery, the reverse blood of the inner needle of the Surflo indwelling needle was confirmed. Then, the inner needle was pulled out and the outer cylinder was placed in the artery and was connected to a syringe filled with the embolic material.

Incidentally, at the time of connection between the outer cylinder and the syringe, the artery contracted and the reverse blood velocity extremely slowed down in some cases. In these cases, if the embolic material had been administered during the contraction, the embolic material could have been administered only to the central side, but not to the site (fingers in this Example) to be treated. For this reason, in these cases, in a state where the syringe was on, the administration was suspended until the syringe was naturally pushed back by the reverse blood, without moving the outer cylinder. This is because such pushback is a sign that the contraction has been released.

(3) Start of Administration of Embolic Material

After connecting the outer cylinder and the syringe, the syringe was pushed to start the administration of the embolic material. The embolic material was administered at a pace of 0.2 g/min. During the administration, reverse blood was frequently confirmed while slowly administering. This is because, if the reverse blood is not frequently confirmed, there is a possibility that the therapeutic agent is administered outside the administration site without knowing that the outer cylinder has been taken off.

(4) End of Administration of Embolic Material

After the start of the administration of the embolic material, the outer cylinder was quickly pulled out at the time when any one or more of the following (A) to (D) was confirmed, and compression hemostasis was performed to terminate the administration of the embolic material.

(A) Heat sensation at a pain site (by the patient's complaint)

(B) Pain different from the pain at the pain site (by the patient's complaint)

(C) Discoloration of the skin of the pain site (by a doctor's visual observation of the appearance)

(D) Detection of the embolic material at the pain site in an X-ray image of Roentgen In the case of this Example, although some of the patients were recognized to have two or more phenomena among (A) to (D), the time period from the time point at which the first phenomena occurred to the time point at which the last phenomena occurred was short (within one minute), and administration of the embolic material was terminated immediately after the time point at which the last phenomena occurred.

(5) Confirmation of Treatment Effect

After the administration, symptoms of the Heberden's nodule were significantly improved. In this Example, although imipenem/cilastatin as the embolus material was used in combination with a contrast agent, when an embolus material other than imipenem/cilastatin was used, even in the case where the contrast agent was not used, an excellent therapeutic effect was exerted by adopting the criteria for the end of the administration in the above administration method.

In addition, by terminating the administration of the embolic material at the above-described timing, it was possible to appropriately prevent excessive administration of the embolic material and outcomes therefrom, including a delayed pain, necrotic color tone change, swelling of the affected area, and the like.

It should be noted that the treatment by the above-mentioned method was not limited to Heberden's nodule, and a good treatment effect was exhibited for patients with another upper limb pain (CM arthritis, Bouchard's nodule, spring finger, rheumatoid arthritis, humerus lateralis epicondylitis (tennis elbow), humerus medial epicondylitis (golf elbow), medial collateral ligament injury, osteochondritis dissecans, elbow synovial plica disorder, humerus medial epicondylus epiphyseal line dysraphism, olecranon epiphyseal line dysraphism, humerus fatigue fracture, radial fatigue fracture, ulnar fatigue fracture, deformed elbow arthritis, elbow-joint synovial inflammation, carpal tunnel syndrome, TFCC injury, and tenosynovitis).

At the time of administration, when the blood flow from the administration site toward the affected area was tilted toward the direction of gravity (for example, when the patient's joint was moved and the blood vessels of the arm and fingers were tilted in the direction of gravity), the above effect tended to be further enhanced.

As the Comparative Example, when the administration of the embolic material was terminated 20 seconds or more after any one or more of the above-mentioned phenomena (A) to (D) was confirmed, adverse events such as swelling of the affected area were observed.

Example 1-2: Treatment of Upper Limb Pain

The embolic material was administered to patients suffering from humerus lateralis epicondylitis (tennis elbow) in the same manner as in the above "Example 1-1", except that, in "(1) Setting of Administration Site of Embolic Material", the brachial artery which flows into the affected area was set as the administration site of the embolic material. Incidentally, the brachial artery at the elbow joint level was set as the administration site.

As a result, the symptoms of humerus lateralis epicondylitis were significantly improved. Such effects were recognized not only in humerus lateralis epicondylitis, but also in patients with another upper limb pain (rheumatoid arthritis, humerus medial epicondylitis (golf elbow), medial collateral ligament injury, osteochondritis dissecans, elbow synovial plica disorder, humerus medial epicondylus epiphyseal line dysraphism, olecranon epiphyseal line dysraphism, humerus fatigue fracture, radial fatigue fracture, ulnar fatigue fracture, deformed elbow arthritis, elbow-joint synovial inflammation, carpal tunnel syndrome, TFCC injury, and tenosynovitis).

At the time of administration, when the blood flow from the administration site toward the affected area was tilted in the direction of gravity (for example, when the patient's joint is moved and the blood vessels of the arm and fingers were tilted toward the direction of gravity), the above effect tended to be further enhanced.

Example 2-1: Treatment of Lower Limb Pain

The embolic material was administered to patients with plantar fasciitis (corresponding to the lower limb pain) in the following manner to confirm an effect thereof.

(1) Setting of Administration Site of Embolic Material

The posterior tibial artery was set as the administration site. This site corresponds to the artery that feeds the pain site.

(2) Puncture to Administration Site (Artery)

The posterior tibial artery was observed with ultrasound waves and the vicinity of the administration site (artery) was anesthetized under ultrasound guidance. After the anesthetic was applied, the artery was punctured with a Surflo indwelling needle (24 G×19 mm) under ultrasound guidance. It should be noted that the ultrasound guidance was performed because there would have been a possibility of damaging nerves in the vicinity of the artery if the puncture had not been performed under ultrasound guidance. In particular, since the posterior tibial artery is adjacent to the posterior tibial nerve, it was effective to perform puncture under ultrasound guidance to prevent nerve damage. After puncturing the artery, the reverse blood of the inner needle of the Surflo indwelling needle was confirmed. Then, the inner needle was pulled out, and the outer cylinder was placed in the artery and was connected to a syringe filled with the embolic material.

At the time of connection between the outer cylinder and the syringe, the artery contracted and the reverse blood velocity slowed down extremely in some cases. In these cases, if the embolic material had been administered during the contraction, the embolic material could have been administered only to the central side, but not to the site (peripheral affected area in this Example) to be treated. For this reason, in these cases, without moving the outer cylinder, in a state where the syringe was on, the administration was suspended until the syringe was naturally pushed back by the reverse blood. This is because such pushback is a sign that the contraction has been released.

(3) Start of Administration of Embolic Material

After connecting the outer cylinder and the syringe, the syringe was pushed to start the administration of the embolic material. The embolic material was administered at a pace of 0.2 g/min. During the administration, reverse blood was frequently confirmed while slowly administering. This is because, if the reverse blood is not frequently confirmed, there is a possibility that the therapeutic agent is administered outside the administration site without knowing that the outer cylinder has been taken off.

(4) End of Administration of Embolic Material

After the start of the administration of the embolic material, the outer cylinder was quickly pulled out at the time when any one or more of the following (A) to (D) was confirmed, and compression hemostasis was performed to terminate the administration of the embolic material.

(A) Heat sensation at a pain site (by the patient's complaint)

(B) Pain different from the pain at the pain site (by the patient's complaint)

(C) Discoloration of the skin of the pain site (by a doctor's visual observation of the appearance)

(D) Detection of the embolic material at the pain site in an X-ray image of Roentgen In the case of this Example, although some of the patients were recognized to have two or more phenomena among (A) to (D), the time period from the time point at which the first phenomena occurred to the time point at which the last phenomena occurred was short (within one minute), and administration of the embolic material was terminated immediately after the time point at which the last phenomena occurred.

(5) Confirmation of Treatment Effect

After the administration, symptoms of the plantar fasciitis were significantly improved. In this Example, although imipenem/cilastatin as the embolus material was used in combination with a contrast agent, when an embolus material other than imipenem/cilastatin was used, even when the contrast agent was not used, an excellent therapeutic effect was exerted by adopting the criteria for the end of the administration in the above administration method.

In addition, by terminating the administration of the embolic material at the above-described timing, it was possible to appropriately prevent excessive administration of the embolic material and the outcomes therefrom, including delayed pain, necrotic color tone change, swelling of the affected area, and the like.

It should be noted that the treatment by the above method was not limited to plantar fasciitis, and a good treatment effect was exhibited for patients with another lower limb pain (Morton's disease, hallux valgus, rheumatoid arthritis, gout, Achilles tendinitis, external tibial bone painful, foot joint synovitis, knee osteoarthritis, patellar tendinitis (jumper's knee), iliotibial band syndrome (runner's knee), pes anserine bursitis, patellofemoral syndrome, infrapatellar fat pad inflammation, synsprint, pain after artificial joint replacement surgery, Osgood disease, and fatigue fracture).

At the time of administration, when the blood flow from the administration site toward the affected area was tilted in the direction of gravity (for example, when having the patient assume the prone position or the lateral position, with the pain site down, or having the patient bend the knee in which a pain is occurring), the above effect tended to be further enhanced.

As the Comparative Example, when the administration of the embolic material was terminated 1 minute or more after any one or more of the above-mentioned phenomena (A) to (D) was confirmed, adverse events such as swelling of the affected area were observed.

Example 2-2: Treatment of Lower Limb Pain

The embolic material was administered to patients having patellar tendinitis (jumper's knee), in the same manner as in the above "Example 2-1", except that, in "(1) Setting of Administration Site of Embolic Material", the superficial femoral artery which flows into the affected area was set as the administration site of the embolic material. The popliteal artery at the level of the knee joint was set as the administration site.

As a result, the symptoms of patellar tendinitis were significantly improved. Such effects were recognized not only in plantar aponeurositis, but also in patients having another lower limb pain (Arthritis rheumatoid arthritis, gout, Achilles tendinitis, external tibial bone painful, foot joint synovitis, knee osteoarthritis, iliotibial band syndrome (runner's knee), pes anserine bursitis, patellofemoral syndrome, infrapatellar fat pad inflammation, synsprint, a pain after artificial joint replacement surgery, Osgood disease, fatigue fracture, and the like).

At the time of administration, when the blood flow from the administration site toward the affected area was tilted in the direction of gravity (for example, when having the patient assume the prone position), the above effect tended to be further enhanced.

The invention claimed is:

1. A method of treatment for pain of an upper limb or a lower limb of a subject in need thereof, the method comprising:

administering to the subject a pain therapeutic agent comprising a particulate embolic material having an average particle size of 10 μm or more and 200 μm or less, wherein the pain therapeutic agent is used by injection administration into an artery of the upper limb or the lower limb, and administration of the pain therapeutic agent is terminated within 5 seconds after a time of confirmation of any one or more of the following (A) to (D):

(A) heat sensation at a pain site;

(B) a pain different from the pain at the pain site;

(C) discoloration of the skin of the pain site; and (D) detection of the embolic material at the pain site in an X-ray image.

2. The method according to claim 1, wherein the upper limb is an entirety from a wrist to fingertips or a part thereof.

3. The method according to claim 1, wherein the upper limb is an entirety from a shoulder to a wrist or a part thereof.

4. The method according to claim 1, wherein the lower limb is an entirety from an ankle to toes or a part thereof.

5. The method according to claim 1, wherein the lower limb is an entirety from a hip joint to an ankle or a part thereof.

6. The method according to claim 1, wherein the pain is pain arising from one or more selected from the group consisting of Heberden's nodule, CM arthropathy, Bouchard's nodule, spring finger, plantar fasciitis, Morton disease, Achilles tendinitis, and hallux valgus.

7. The method according to claim 1, wherein the pain is pain arising from one or more selected from the group consisting of rheumatoid arthritis, humerus lateralis epicondylitis (tennis elbow), humerus medial epicondylitis (golf elbow), medial collateral ligament injury, osteochondritis dissecans, elbow synovial plica disorder, humerus medial epicondylus epiphyseal line dysraphism, olecranon epiphyseal line dysraphism, humerus fatigue fracture, radial fatigue fracture, ulnar fatigue fracture, deformed elbow arthritis, elbow-joint synovial inflammation, carpal tunnel syndrome, TFCC injury, tenosynovitis, gout, Achilles tendinitis, external tibial bone painful, foot joint synovitis, knee osteoarthritis, patellar tendinitis (jumper's knee), iliotibial band syndrome, pes anserine bursitis, patellofemoral syndrome, infrapatellar fat pad inflammation, synsprint, pain after artificial joint replacement surgery, Osgood disease, and fatigue fracture.

8. The method according to claim 1, wherein the injection administration is performed in a state in which a blood flow to an affected area is tilted more toward a direction of gravity rather than a horizontal plane.

9. The method according to claim 1, wherein the upper limb is a part other than a shoulder joint.

10. The method according to claim 2, wherein the pain is pain arising from one or more selected from the group consisting of Heberden's nodule, CM arthropathy, Bouchard's nodule, spring finger, plantar fasciitis, Morton disease, Achilles tendinitis, and hallux valgus.

11. The method according to claim 2, wherein the injection administration is performed in a state in which a blood flow to an affected area is tilted more toward a direction of gravity rather than a horizontal plane.

12. The method according to claim 1, wherein the pain therapeutic agent is administered to an artery that feeds the pain site, the artery being within 10 centimeters upstream from the pain site.

13. The method according to claim 8, wherein the blood flow from the administration site to the affected area is tilted by 20° or more with respect to a horizontal plane.

14. The method according to claim 8, wherein the blood flow from the administration site to the affected area is tilted by 45° or more with respect to a horizontal plane.

15. The method according to claim 1, wherein the administration of the pain therapeutic agent is terminated based on two or more of (A) to (D) within 5 seconds after a time at which a last one of the two or more of (A) to (D) is confirmed, and a time period starting from a first time at which a first one of the two or more of (A) to (D) is confirmed and ending at a time at which the last one of the two or more of (A) to (D) is confirmed is one minute or less.

16. The method according to claim 1, wherein the administration of the pain therapeutic agent is terminated based on confirmation of discoloration of the skin of the pain site.

17. The method according to claim 1, wherein the administration of the pain therapeutic agent is terminated based on confirmation of a pain different from the pain at the pain site.

18. The method according to claim 1, wherein the administration of the pain therapeutic agent is terminated based on confirmation of heat sensation at the pain site.

19. The method according to claim 1, wherein the administering of the pain therapeutic agent comprises puncturing the artery with an injection needle and administering the pain therapeutic agent from a syringe, and, when the syringe containing the pain therapeutic agent is connected to the administration site and reverse blood velocity slows, suspending the administration of the pain therapeutic agent until the syringe is naturally pushed back by the reverse blood.

* * * * *